United States Patent [19]

Brown et al.

[11] 4,145,546
[45] Mar. 20, 1979

[54] 4-PYRIMIDONE COMPOUNDS

[75] Inventors: Thomas H. Brown; Graham J. Durant, both of Welwyn Garden City; John C. Emmett, Codicote; Charon R. Ganellin, Welwyn Garden City, all of England

[73] Assignee: Smith Kline & French Laboratories Limited, Welwyn Garden City, England

[21] Appl. No.: 835,234

[22] Filed: Sep. 21, 1977

Related U.S. Application Data

[63] Continuation-in-part of Ser. No. 726,885, Sep. 27, 1976, abandoned.

[51] Int. Cl.$^2$ .......................................... C07D 239/56
[52] U.S. Cl. ..................... 544/310; 544/309; 544/320; 544/321; 424/251; 544/311; 544/314; 544/319
[58] Field of Search ................... 260/251 R; 544/310, 544/309

[56] References Cited

U.S. PATENT DOCUMENTS 3,932,644   1/1976   Durant et al. ..................... 424/263

FOREIGN PATENT DOCUMENTS 814032   3/1973   Belgium.

OTHER PUBLICATIONS

Aroyan et al., Chem. Abst., 68: 12933y (1968).
Aroyan et al., Chem Abst. 72: 21652r (1970).
Chang et al., Chem. Abst. 52: 2024a.
Johnson et al., Chem. Abst. 3: 27055.
Hurst et al., J. Chem. Soc. 7116–7119 (1965).

*Primary Examiner*—Raymond V. Rush
*Assistant Examiner*—Lisa Jones
*Attorney, Agent, or Firm*—Joan S. Keps; Richard D. Foggio; William H. Edgerton

[57] ABSTRACT

The compounds are substituted isocytosines which are histamine $H_2$-antagonists. Two specific compounds of the present invention are 2-[2-(5-methyl-4-imidazolylmethylthio)-ethylamino]-5-(3-methoxybenzyl)-4-pyrimidone and 2-[2-(5-methyl-4-imidazolylmethylthio)ethylamino]-5-benzyloxy-4-pyrimidone.

3 Claims, No Drawings

4-PYRIMIDONE COMPOUNDS

This invention relates to pharmacologically active compounds, to pharmaceutical compositions containing these compounds and to methods of blocking histamine $H_2$-receptors by administering these compounds. The compounds of the invention can exist as acid addition salts but, for convenience, reference will be made throughout this specification to the parent compounds.

Many physiologically active substances elicit their biological actions by interaction with specific sites known as receptors. Histamine is such a substance and has a number of biological actions. Those biological actions of histamine which are inhibited by drugs commonly called "antihistamines" of which mepyramine, diphenhydramine and chloropheniramine are examples, are mediated through histamine $H_1$-receptors (Ash and Schild, Brit. J. Pharmac. Chemother., 27, 427, (1966)), and drugs with this activity are hereinafter referred to as histamine $H_1$-antagonists. However, other of the biological actions of histamine are not inhibited by histamine $H_1$-antagonists and actions of this type which are inhibited by a compound described by Black et al. (Nature, 236, 385, (1972)) and called burimamide are mediated through receptors which are defined by Black et al. as histamine $H_2$-receptors. Thus histamine $H_2$-receptors may be defined as those histamine receptors which are not blocked by mepyramine but are blocked by burimamide. Compounds which block histamine $H_2$-receptors are referred to as histamine $H_2$-antagonists.

Blockade of histamine $H_2$-receptors is of utility in inhibiting the biological actions of histamine which are not inhibited by histamine $H_1$-antagonists. Histamine $H_2$-antagonists are therefore useful, for example, as inhibitors of gastric acid secretion, as anti-inflammatory agents and as agents which act on the cardiovascular system, for example as inhibitors of the effects of histamine on blood pressure. In the treatment of certain conditions, for example, inflammation and in inhibiting the actions of histamine on blood pressure, a combination of histamine $H_1$- and $H_2$-antagonists is useful. The compounds of this invention have both histamine $H_1$-antagonist and histamine $H_2$-antagonist activity, and are useful in the treatment of conditions wherein histamine $H_2$-antagonists are useful and conditions wherein a combination of histamine $H_1$- and $H_2$-antagonists are useful.

Throughout this specification by the terms "lower alkyl" and "lower alkoxy" we mean groups containing from 1 to 4 carbon atoms.

In U.S. Pat. No. 3,932,644, compounds of Formula 1 and tautomers thereof are described as histamine $H_2$-antagonists.

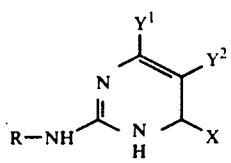

FORMULA 1

In Formula 1, R represents a group of the structure shown in Formula 2:

Het-CH$_2$Z(CH$_2$)$_n$-      FORMULA 2 wherein Het is a nitrogen-containing heterocyclic ring such as imidazole, pyridine, thiazole, isothiazole or thiadiazole, which ring is optionally substituted by lower alkyl, amino, hydroxy or halogen; Z is sulphur or a methylene group; and n is 2 or 3; X is oxygen or sulphur; $Y^1$ and $Y^2$, which may be the same or different, are hydrogen, lower alkyl, phenyl or benzyl.

We have now found a group of substituted isocytosines which are histamine $H_2$-antagonists and have histamine $H_1$-antagonist activity as well as histamine $H_2$-antagonist activity.

This group of substituted isocytosines which are the compounds of this invention is represented by Formula 3:

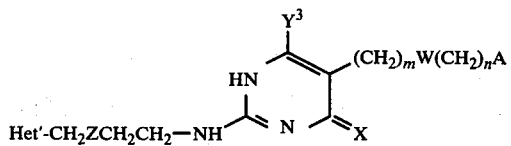

FORMULA 3 wherein Het' is a 2- or 4-imidazolyl ring optionally substituted by lower alkyl (preferably methyl), halogen (preferably chlorine or bromine), trifluoromethyl or hydroxymethyl, a 2-pyridyl ring optionally substituted by lower alkyl (preferably methyl), lower alkoxy (preferably methoxy), halogen (preferably chlorine or bromine), amino or hydroxy, a 2-pyridyl ring which is disubstituted by lower alkoxy groups, or which has a phenyl, carbocyclic or cyclic ether ring containing two oxygen atoms fused to it, a 2-thiazolyl ring, a 3-isothiazole ring optionally substituted by chlorine or bromine, a 3-(1,2,5)thiadiazolyl ring optionally substituted by chlorine or bromine, or a 2-(5-amino-1,3,4-thiadiazolyl)ring; Z is sulphur or a methylene group; X is oxygen or sulphur, W is methylene, oxygen or sulphur; m and n are such that their sum is from 1 to 4 when W is oxygen or sulphur, or from 0 to 4 when W is methylene; A is a 1- or 2-naphthyl ring, a 2,3-dihydro-1,4-benzodioxinyl or a 1,3-benzodioxolyl ring, a phenyl ring substituted with one or more lower alkyl, lower alkoxy, halogen, arylalkoxy (preferably benzyloxy), hydroxy, loweralkoxyloweralkoxy, trifluoromethyl, di(loweralkyl)amino, phenoxy, halophenoxy, lower alkoxyphenoxy, phenyl, halophenyl or lower alkoxyphenyl groups and when -(CH$_2$)$_m$W(CH$_2$)$_n$- is not a methylene group, A may also be phenyl; and $Y^3$ is hydrogen or lower alkyl. Preferably Het' is a 2-thiazolyl, 5-methyl-4-imidazolyl, 5-bromo-4-imidazolyl, 3-bromo-2-pyridyl, 3-chloro-2-pyridyl, 3-methoxy-2-pyridyl or 3-hydroxy-2-hydroxy-2-pyridyl ring. Preferably Z is sulphur. Preferably X is oxygen. Preferably $Y^3$ is hydrogen. Preferably A is a phenyl group substituted by one or more lower alkoxy groups, or is a 2,3-dihydro-1,4-benzodioxinyl or 1,3-benzodioxolyl ring, as compounds of Formula 3 wherein A has these meanings have favourable solubility properties when compared to the general group of compounds of formula 3.

A preferred group of compounds is that wherein m and n are O and W is methylene. Another preferred group of compounds is that wherein m is O, n is 1 and W is oxygen.

Some specific preferred compounds which fall within the particular group of compounds of Formula 3 are:

2-[2-(5-methyl-4-imidazolylmethylthio)ethylamino]-5-(4-chlorobenzyl)-4-pyrimidone
2-[2-(2-thiazolylmethylthio)ethylamino]-5-(4-chlorobenzyl)-4-pyrimidone
2-[2-(3-bromo-2-pyridylmethylthio)ethylamino]-5-(4-chlorobenzyl)-4-pyrimidone
2-[2-(5-methyl-4-imidazolylmethylthio)ethylamino]-5-(4-chlorobenzyl)-6-methyl-4-pyrimidone
2-[2-(5-methyl-4-imidazolylmethylthio)ethylamino]-5-(3-chlorobenzyl)-4-pyrimidone
2-[2-(5-methyl-4-imidazolylmethylthio)ethylamino]-5-(3,4-dichlorobenzyl)-4-pyrimidone
2-[2-(5-methyl-4-imidazolylmethylthio)ethylamino]-5-(4-methoxybenzyl)-4-pyrimidone
2-[2-(5-methyl-4-imidazolylmethylthio)ethylamino]-5-(4-methylbenzyl)-4-pyrimidone
2-[2-(5-methyl-4-imidazolylmethylthio)ethylamino]-5-(2-phenylethyl)-4-pyrimidone
2-[2-(5-methyl-4-imidazolylmethylthio)ethylamino]-5-(2-phenylethyl)-6-methyl-4-pyrimidone
2-[2-(5-methyl-4-imidazolylmethylthio)ethylamino]-5-benzyloxy-4-pyrimidone
2-[2-(5-methyl-4-imidazolylmethylthio)ethylamino]-5-(3-methoxybenzyl)-4-pyrimidone
2-[2-(5-methyl-4-imidazolylmethylthio)ethylamino]-5-(2-chlorobenzyl)-4-pyrimidone
2-[2-(5-methyl-4-imidazolylmethylthio)ethylamino]-5-(4-phenylbutyl)-4-pyrimidone
2-[2-(5-methyl-4-imidazolylmethylthio)ethylamino]-5-(5-(1,3-benzodioxolyl)methyl)-4-pyrimidone
2-[2-(5-methyl-4-imidazolylmethylthio)ethylamino]-5-(3-ethoxybenzyl)-4-pyrimidone
2-[2-(5-methyl-4-imidazolylmethylthio)ethylamino]-5-(3-benzyloxybenzyl)-4-pyrimidone
2-[2-(5-methyl-4-imidazolylmethylthio)ethylamino]-5-(1-naphthylmethyl)-4-pyrimidone.

The compounds of Formula 3 are shown and described as 4-one and 4-thione derivatives and these derivatives exist in equilibrium with the corresponding 6-one and 6-thione tautomers. These compounds also exist to a lesser extent as the mercapto and hydroxy tautomers and the pyrimidine ring may also exist in the following tautomeric forms:

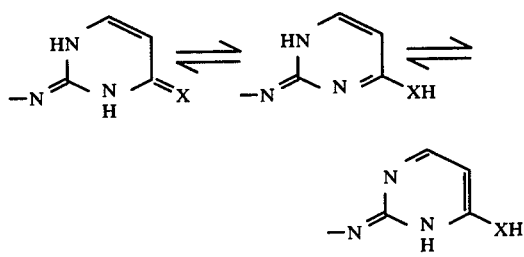

Het' may also exist in several tautomeric forms, and it will be understood that all these tautomeric forms are within the scope of the present invention. The compounds of this invention may be prepared by treating an amine of Formula 4:

Het'-CH$_2$ZCH$_2$CH$_2$NH$_2$   Formula 4 wherein Het' and Z are as defined in Formula 3, with a compound of Formula 5:

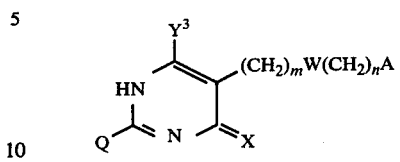

Formula 5 wherein X, Y$^3$, m, W, n and A are as defined in Formula 3 and Q is loweralkylthio, benzylthio, halogen, or other reactive grouping which is conveniently displaced with an amine. Preferably this reaction is carried out in the absence of a solvent at about 150° C. or in the presence of a solvent, such as refluxing pyridine. The intermediates of Formula 5 are also objects of this invention.

The intermediates of Formula 5 wherein W is methylene, Y$^3$ is hydrogen and Q is loweralkylthio (shown as Formula 8) may be prepared according to Scheme 1:

Scheme 1

(wherein A is as defined in Formula 3 and a is 0 to 4 and Alk is lower alkyl)

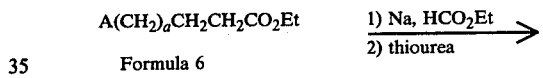

Formula 6

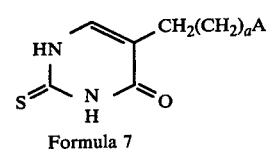

Formula 7 alkyl halide or sulphate

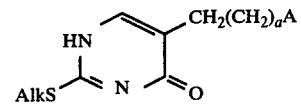

Formula 8

The esters of Formula 6 wherein a is 0 may be prepared by condensing a substituted benzaldehyde with malonic acid, and hydrogenating and esterifying the product.

The intermediates of Formula 5 wherein W is methylene, Y$^3$ is loweralkyl and Q is loweralkylthio (shown as Formula 9) may be prepared according to Scheme 2:

Scheme 2

(wherein A is as defined in Formula 3, a is 0 to 4, Hal is chlorine or bromine, and Alk is lower alkyl)

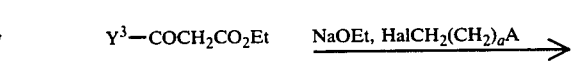

-continued

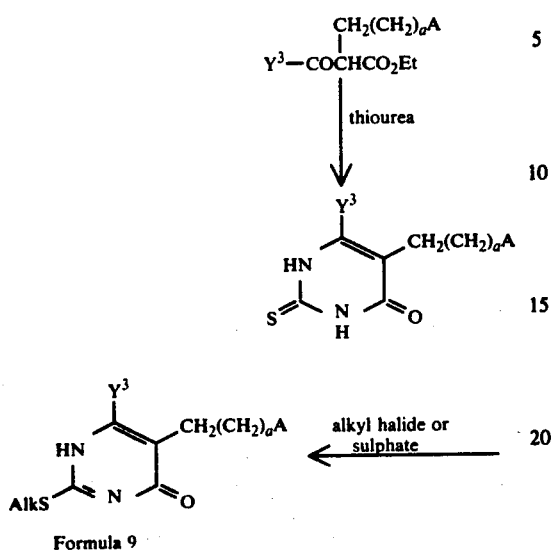

Formula 9

The intermediates of Formula 5 wherein Q is halogen (shown as Formula 11) may be prepared according to Scheme 3:

Scheme 3

(wherein A and $Y^3$ are as defined in Formula 3, a is 0 to 4 and Hal is chlorine or bromine.

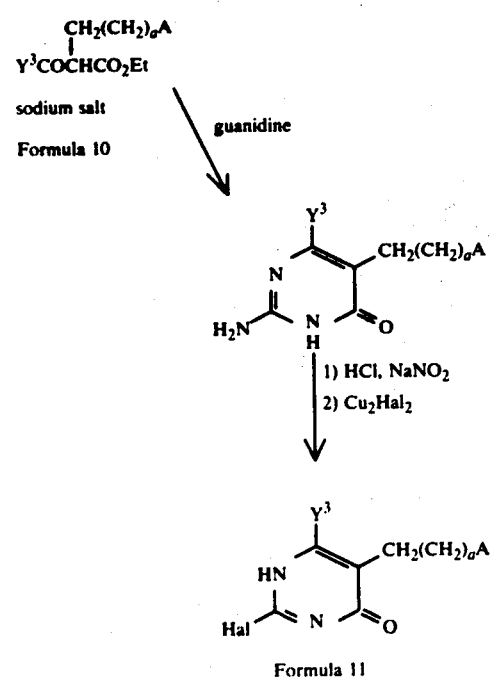

Formula 11

The compounds of Formula 10 wherein $Y^3$ is hydrogen may be prepared from a compound of Formula 6, sodium and ethyl formate, and the compounds of Formula 10 wherein $Y^3$ is lower alkyl may be prepared as shown in Scheme 2.

The intermediates of Formula 5 wherein W is oxygen or sulphur may be prepared by the following methods:

(a) m is 0

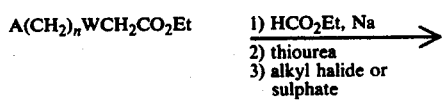

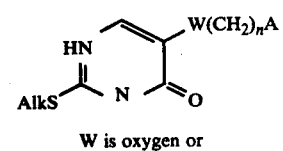

W is oxygen or sulphur (b) m is 1

These compounds may be prepared by the route:

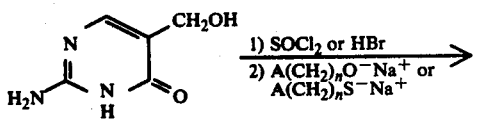

W is oxygen or sulphur

W is oxygen or sulphur or alternatively, from ethyl 4-benzyloxybutyrate, or a similar protected derivative of ethyl 4-hydroxybutyrate, by a process analogous to that outlined in Scheme 1, followed successively by deprotection, treatment with thionyl cloride, and treatment with the sodium derivative of $A(CH_2)_nOH$ or $A(CH_2)_nSH$.

(c) m is 2 to 4

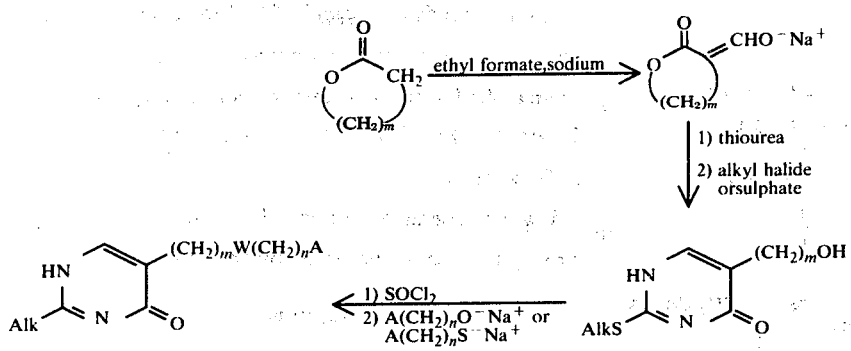

W is oxygen or sulphur
m is 2 to 4

Compounds of Formula 3 wherein X is sulphur may be prepared by treating the compounds of Formula 3 wherein X is oxygen with phosphorus pentasulphide in a solvent such as pyridine.

The compounds of Formula 3 block histamine $H_2$-receptors, that is they inhibit the biological actions of histamine which are not inhibited by histamine $H_1$-antagonists such as mepyramine but are inhibited by burimamide. For example, the compounds of this invention have been found to inhibit histamine-stimulated secretion of gastric acid from the lumen-perfused stomachs of rats anaesthetized with urethane, at doses of from 0.5 to 16 micromoles per kilogram intravenously. Many of the compounds of the present invention produce at least 50% inhibition in this test at a dose of from 1 to 10 micromoles per kilogram. This procedure is referred to in the above-mentioned paper of Ash and Schild. The activity of these compounds as histamine $H_2$-antagonists is also demonstrated by their ability to inhibit other actions of histamine which, according to the above-mentioned paper of Ash & Schild, are not mediated by histamine $H_1$-receptors. For example, they inhibit the actions of histamine on the isolated guinea pig atrium and isolated rat uterus.

The compounds of this invention inhibit the basal secretion of gastric acid and also that stimulated by pentagastrin or by food.

In addition, the compounds of this invention show anti-inflammatory activity in conventional tests such as the rat paw oedema test, where the oedema is induced by an irritant, the rat paw volume is reduced by subcutaneous injection of doses of about 500 micromoles/kg. of a compound of Formula 3. In a conventional test, such as the measurement of blood pressure in the anaesthetised cat, the action of the compounds of this invention in inhibiting the vasodilator action of histamine can also be demonstrated. The level of activity of the compounds of this invention is illustrated by the effective dose producing 50% inhibition of gastric acid secretion in the anaesthetised rat (which for many of the compounds of Formula 3 is from 1 to 10 micromoles per kilogram) and the dose producing 50% inhibition of histamine-induced tachycardia in the isolated guinea pig atrium, (which for many of the compounds of Formula 3, is below $10^{-5}M$).

The compounds of Formula 3 also block histamine $H_1$-receptors, that is they inhibit the biological actions of histamine which are inhibited by mepyramine, diphenhydramine and chlorpheniramine. For example the compounds of this invention have been found to inhibit the action of histamine in the isolated guinea-pig ileum. They inhibit the histamine-stimulated contractions of the guinea pig ileum at doses of about $10^{-5}$ Molar.

For therapeutic use, the pharmacologically active compounds of the present invention will normally be administered as a pharmaceutical composition comprising as the or an essential active ingredient at least one such compound in the basic form or in the form of an addition salt with a pharmaceutically acceptable acid and in association with a pharmaceutical carrier therefor. Such addition salts include those with hydrochloric, hydrobromic, hydriodic, sulphuric and maleic acids and may conveniently be formed from the corresponding bases of Formula 3 by standard procedures, for example by treating the base with an acid in a lower alkanol or by the use of iron exchange resins to form the required salt either directly from the base or from a different addition salt.

Pharmaceutical compositions comprising a pharmaceutical carrier and a compound of Formula 3 or a pharmaceutically acceptable acid addition salt thereof and methods of blocking histamine $H_2$-receptors which comprise administering to an animal a compound of Formula 3 or a pharmaceutically acceptable acid addition salt thereof are also objects of this invention. The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like.

A wide variety of pharmaceutical forms can be employed. Thus, if a solid carrier is used, the preparation can be tableted, placed in a hard gelatin capsule in powder or pellet form, or in the forms of a troche or lozenge. The amount of solid carrier will vary widely but preferably will be from about 25 mg to about 1 g. If a liquid carrier is used, the preparation may be in the form of a syrup, emulsion, soft gelatin capsule, sterile injectable liquid contained for example in an ampoule, or an aqueous or nonaqueous liquid suspension.

The pharmaceutical compositions are prepared by conventional techniques involving procedures such as mixing, granulating and compressing or dissolving the ingredients as appropriate to the desired preparation.

The active ingredient will be present in the compositions in an effective amount to block histamine $H_2$-receptors. The route of administration may be oral or parenteral.

Preferably, each dosage unit will contain the active ingredient in an amount of from about 50 mg to about 250 mg.

The active ingredient will preferably be administered one to six times per day. The daily dosage regimen will preferably be from about 150 mg to about 1500 mg.

Advantageously the composition will be made up in a dosage form appropriate to the desired mode of administration for example, as a tablet, capsule, injectable solution or as a cream or ointment for topical application.

The invention is illustrated but in no way limited by the following Examples in which all temperatures are in degrees Centigrade:

EXAMPLE 1

2-[2-(5-Methyl-4-imidazolylmethylthio)ethylamino]-5-(4-chlorobenzyl)-4-pyrimidone (i) A solution of 5-(4-chlorobenzyl)-2-thiouracil (50.5 g), methyl iodide (28.4 g) and sodium hydroxide (8.2 g) in water (200 ml) and ethanol (400 ml) was stirred at 60° for 30 minutes then allowed to cool. The crystalline product was filtered and washed with water to give 5-(4-chlorobenzyl)-2-methylthio-4-pyrimidone (48.6 g), m.p. 193°–194° (methanol/ethanol).

(ii) An intimate mixture of 5-(4-chlorobenzyl)-2-methylthio-4-pyrimidone (17.7 g) and 2-(5-methyl-4-imidazoylmethylthio-ethylamine (11.4 g) was heated at 145°–150° for 5 hours. After cooling, the reaction mixture was triturated with water to give the free base, which was separated by decantation and recrystallised from methanol to give 2-[2-(5-methyl-4-imidazolylmethylthio)ethylamino]-5-(4-chlorobenzyl)-4-pyrimidone m.p. 204.5°–206°.

(Found: C, 55.45; H, 5.2; N, 18.0: S, 8.3 . Cl, 8.9; $C_{18}H_{22}ClN_5OS$ requires; C, 55.45; H, 5.2; N, 18.0; S, 8.2: Cl, 9.1%).

EXAMPLE 2

2-[2-(5-Methyl-4-imidazolylmethylthio)ethylamino]-5-(2-phenyleth-4-pyrimidone dihydrochloride 5-(2-Phenylethyl)-2-thiouracil (1.8 g) was converted into 5-phenylethyl-2-methylthio-4-pyrimidone (m.p. 160°–161° ex ethanol) by the method described in Example 1(i). Reaction of this pyrimidone (1.55g) with 2-(5-methyl-4-imidazolylmethylthio)-ethylamine (1.1 g) by the method described in Example 1(ii) gave an oil which was dissolved in 2N hydrochloric acid, the solution evaporated to dryness and the residue recrystallised from methanol to give 2-[2-(5-methyl-4-imidazolylmethylthio)-ethylamino]-5-(2-phenylethyl)-4-pyrimidone dihydrochloride, m.p. 214°–218°.

(Found: C, 51.3; H, 5.6; N, 15.8: S, 7.1; Cl, 15.8: $C_{19}H_{23}N_5OS$. 2 HCl requires: C, 51.6; H, 5.7: N, 15.8; S, 7.25; Cl, 16.0%).

EXAMPLE 3

2-[2-(5-Methyl-4-imidazolylmethylthio)ethylamino]-5-(4-methylbenzyl)-4-pyrimidone dihydrochloride 5-(4-Methylbenzyl)-2-thiouracil (4.65 g) was converted into 5-(4-methylbenzyl)-2-methylthio-4-pyrimidone (m.p. 208.5°–211° ex methanol/ethanol) by the method described in Example 1(i). Reaction of this pyrimidone (1.6 g) with 2-(5-methyl-4-imidazolylmethylthio)ethylamine (1.2 g) by the method described in Example 1(ii) and acidification with dilute ethanolic hydrogen chloride followed by evaporation to dryness and recrystallisation from ethanol gave 2-[2-(5-methyl-4-imidazolylmethylthio)ethylamino]-5-(4-methylbenzyl)-4-pyrimidone dihydrochloride, m.p. 197°–198.5°.

(Found: C, 51.9; H, 5.7; N, 15.9: S, 7.3: Cl, 15.4; $C_{19}H_{23}N_5OS$. 2HCl. requires: C, 51.6; H, 5.7; N, 15.8; S, 7.25; Cl, 16.0%).

In a similar manner 2-[2-(5-methyl-4-imidazlylmethylthio)-ethylamino]-5-(3-methylbenzyl)-4-pyrimidone dihydrochloride m.p. 203.5°–205° (ex ethanol) may be prepared from 5-(3-methylbenzyl)-2-thiouracil.

EXAMPLE 4

2-[2-(5-Methyl-4-imidazolylmethylthio)ethylamino]-5-(3-chlorobenzyl)-4-pyrimidone dihydrochloride (i) Ethyl 3-(3-chlorophenyl) propionate (39.3 g) and ethyl formate (14.9 g) were added over a period of 6 hours to a stirred mixture of sodium wire (4.25 g) and dry ether (110 ml) cooled with an ice-salt bath. The mixture was stirred for 18 hours at room temperature and evaporated to dryness. The residue was refluxed for 7 hours with thiourea (14.05 g) and ethanol (100 ml). The mixture was evaporated to dryness and the residue was dissolved in water. Acetic acid was added until the mixture had pH 4. The white precipitate was filtered and washed to give 5-(3-chlorobenzyl)-2-thiouracil, m.p. 192°–195° (ethanol).

(ii) 5-(3-Chlorobenzyl)-2-thiouracil (3.1 g) was converted into 5-(3-chlorobenzyl)-2-methylthio-4-pyrimidone, m.p. 178.5°–180.5° (ethanol) by the method described in Example 1(i) and this latter compound (1.8 g) was reacted with 2-(5-methyl-4-imidazolylmethylthio)ethylamine (1.14 g) as described in Example 1(ii) to give a residue which was treated with ethanolic hydrogen chloride to give 2-[2-(5-methyl-4-imidazolylmethylthio)ethylamino]-5-(3-chlorobenzyl)-4-pyrimidone dihydrochloride, m.p. 212.5°–216° (crystallised from ethanol).

(Found: C, 46.8; H, 4.7; N, 14.9: S, 6.9; Cl, 22.7. $C_{18}H_{20}Cl\ N_5OS$. 2 HCl. requires: C, 46.7; H, 4.8: N, 15.1; S, 6.9; Cl, 23.0%).

EXAMPLE 5

2-[2-(5-Methyl-4-imidazolylmethylthio)ethylamino]-5-(3,4-dichlorobenzyl)-4-pyrimidone dihydrochloride (i) Ethyl 3(3,4-dichlorophenyl)propionate (48.9 g) was converted into 5-(3,4-dichlorobenzyl)-2-thiouracil m.p. 232.5°–233.5° (ex methanol/ethanol) by the procedure of Example 4(i).

(ii) 5-(3,4-Dichlorobenzyl)-2-thiouracil (5.7 g) was converted into 5-(3,4-dichlorobenzyl)-2-methylthio-4-pyrimidone, m.p. 216°–218° (acetic acid) by the procedure of Example 1(i).

(iii) 5-(3,4-Dichlorobenzyl)-2-methylthio-4-pyrimidone (2.1 g) was reacted with 2-(5-methyl-4-imidazolylmethylthio)ethylamine (1.2 g) by the procedure of Example 3 to give 2-[2-(5-methyl-4-imidazolylmethylthio)ethylamino]-5-(3,4-dichlorobenzyl)-4-pyrimidone dihydrochloride, m.p. 235.5°–238.5° (aqueous methanol)

(Found: C, 43.3; H, 4.3; N, 13.8; S, 6.4; Cl, 27.8; $C_{18}H_{19}Cl_2N_5OS.2HCl$. requires; C, 43.5; H, 4.3; N, 14.1; S, 6.45; Cl, 28.5%).

EXAMPLE 6

2-[2-(2-thiazolylmethylthio)ethylamino]-5-(4-chlorobenzyl)-4-pyrimidone monohydrochloride An intimate mixture of 5-(4-chlorobenzyl)-2-methylthio-4-pyrimidone (1.36 g) and 2-(2-thiazolylmethylthio)ethylamine (0.9 g) was heated at 130°–135° for 3½ hours. After cooling the reaction mixture was treated with 2N hydrochloric acid. Evaporation to dryness followed by recrystallisation from isopropanol/methanol gave 2-[2-(2-thiazolyl-methylthio)-ethylamino]-5-(4-chlorobenzyl)-4-pyrimidone monohydrochloride, m.p. 172.5°–174.5°.

Found: C, 47.4; H, 4.3; N, 13.0; S, 14.7; Cl, 16.5; $C_{16}H_{18}Cl\ N_4OS_2.HCl$. requires; C, 47.55; H, 4.2; N, 13.05; S, 14.9; Cl, 16.5%).

EXAMPLE 7

2-[2-(5-Methyl-4-imidazolylmethylthio)ethylamino]-5-(4-methoxybenzyl)-4-pyrimidone dihydrochloride An intimate mixture of 5-(4-methoxybenzyl(-2-methylthio-4-pyrimidone (3.0 g) and 2-(5-methyl-4-imidazolylmethylthio)-ethylamine (1.95 g) was heated at 135°–140° with frequent stirring for 6 hours. After cooling, the reaction mixture was triturated with hot water, filtered, washed with dry ether and dissolved in propan-2-ol. The solution was acidified with dilute ethanolic hydrogen chloride, evapoated to dryness, and the residue recrystallised from ethanol to give 2-[2-(5-methyl-4-imidazolylmethylthio)ethylamino]-5-(4-methoxybenzyl)- 4-pyrimidone dihydrochloride m.p. 198°–200°.

(Found: C, 49.0; H, 5.5; N, 15.0; S, 6.9; Cl, 14.7; $C_{19}H_{23}N_5O_2S.2HCl$ requires; C, 49.8; H, 5.5; N, 15.3; S, 7.0; Cl, 15.5%).

EXAMPLE 8

2-[2-(5-Methyl-4-imidazolylmethylthio)ethylamino]-5-(4-chlorobenzyl)-6-methyl-4-pyrimidone dihydrochloride (i) 5-(4-Chlorobenzyl)-6-methyl-2-thiouracil was methylated with methyl iodide as described in Example 1 (i) to give 5-(4-chlorobenzyl)-6-methyl-2-methylthio-4-pyrimidone (m.p. 248°–251°).

Found: C, 55.6; H, 4.7; N, 10.0; S, 11.4: $C_{13}H_{13}ClN_2OS$ requires: C, 55.3; H, 4.6; N, 9.9; S, 11.4%).

(ii) Reaction of 5-(4-chlorobenzyl)-6-methyl-2-methylthio-4-pyrimidone (1.95 g) with 2-(5-methyl-4-imidazolylmethylthio)ethylamine (1.19 g) by the method described in Example I (ii) gave the title compound, m.p. 203°–206.5°. (Crystallised from ethanol).

(Found: C, 47.7; H, 5.1; N, 14.4; S, 6.6; Cl, 21.3; $C_{19}H_{22}ClN_5OS.2HCl$ requires: C, 47.9; H, 5.1; N, 14.7; S, 6.7; Cl, 22.3%).

EXAMPLE 9

2-[2-(3-Bromo-2-pyridylmethylthio)ethylamino]-5-(4-chlorobenzyl)-4-pyrimidone monohydrochloride 5-(4-Chlorobenzyl)-2-methylthio-4-pyrimidone (1.2 g) was reacted with 2-(3-bromo-2-pyridylmethylthio)ethylamine (1.1 g) according to the procedure of Example 2. The reaction mixture was acidified with dilute ethanolic hydrogen chloride, evaporated to dryness and the residue recrystallised from ethanol/water to give 2-[2-(3-bromo-2-pyridylmethylthio)ethylamino]-5-(4-chlorobenzyl)-4-pyrimidone monohydrochloride, m.p. 215°–218° (decomposes).

(Found: C, 45.4; H, 3.8; N, 11.1; S, 6.3; $C_{12}H_{18}Br\ Cl\ N_4OS.H$ requires: C, 45.4; H, 3.8; N, 11.2; S, 6.4%).

EXAMPLE 10

2-[2-(5-Methyl-4-imidazolylmethylthio)ethylamino]-5-(2-phenylethyl)-6-methyl-4-pyrimidone (1) Ethyl α-(phenylethyl)acetoacetate (23.4g) and thiourea (10.65g) were added to a solution of sodium ethoxide in ethanol (100 ml) prepared from sodium (4.6g). The mixture was refluxed for 5½ hours and evaporated to dryness. The solid residue was dissolved in water and acetic acid was added to pH 4. The white precipitate was filtered off and recrystallised from ethanol to give 5-(2-phenylethyl)-6-methyl-2-thiouracil m.p. 210°–214°.

(2) Substitution of 5-(2-phenylethyl)-6-methyl-2-thiouracil for 5-(4-chlorobenzyl)-2-thiouracil in the general procedure of Example 1 gave the title compound m.p. 222.5°–224.5° (methanol)

Found: C, 62.75; H, 6.5; N, 18.1; S, 8.3; $C_{20}H_{25}N_5OS$ requires C, 62.6; H, 6.6; N, 18.2; S, 8.4%).

EXAMPLE 11

2-[2-(5-Methyl-4-imidazolylmethylthio)ethylamino]-5-benzyloxy-4-pyrimidone dihydrochloride (i) Ethyl benzyloxyacetate (60.0 g) was converted into 5-benzyloxy-2-thiouracil m.p. 240°–241° (ex. acetonitrile/ethyl acetate, 1:1) by the procedure of Example 4(i).

(ii) 5-Benzyloxy-2-thiouracil (10.0 g) was converted into 5-benzyloxy-2-methylthio-4-pyrimidone m.p. 184°–185° (ex methanol) by the procedure of Example 1(i).

(iii) 5-Benzyloxy-2-methylthio-4-pyrimidone (4.10 g) was reacted with 2-(5-methyl-4-imidazolyl)ethylamine (2.83 g) by the procedure of Example 3 to give 2-[2-(5-methyl-4-imidazolylmethylthio)ethylamino]-5-benzyloxy-4-pyrimidone dihydrochloride, m.p. 161°–162° (ethanol).

EXAMPLE 12

2-[2-(5-Methyl-4-imidazolylmethylthio)ethylamino]-5-(3-methoxybenzyl)-4-pyrimidone dihydrochloride 5-(3-Methoxybenzyl)-2-thiouracil (16.1 g) was converted into 5-(3-methoxybenzyl)-2-methylthio-4-pyrimidone, m.p. 143°–144° C. (ex ethanol) by the procedure of Example 1(i).

5-(3-Methoxybenzyl)-2-methylthio-4-pyrimidone (3.0 g) was reacted with 2-(5-methyl-4-imidazolylmethylthio)ethylamine (2.1 g) as described in Example 1(ii), to give a residue, which, on treatment with ethanolic hydrogen chloride gave 2-[2-(5-methyl-4-imidazolylmethylthio)ethylamino]-5-(3-methoxybenzyl)-4-pyrimidone dihydrochloride, m.p. 173°–175.5° (ex ethanol).

(Found: C, 49.6; H, 5.3; N, 15.1; S, 7.1; Cl, 15.8; $C_{19}H_{25}Cl_2N_5O_2S$ requires: C, 49.8; H, 5.5; N, 15.3; S, 7.0; Cl, 15.5%). Treatment of this dihydrochloride with aqueous sodium bicarbonate, extraction of the mixture with ethyl acetate and evaporation of the organic extracts gives the free base which is converted into 2-[2-(5-methyl-4-imidazolylmethylthio)ethylamino]-5-(3-methoxybenzyl)-4-pyrimidone dihydrobromide by treatment with two equivalents of hydrobromic acid.

EXAMPLE 13

2-[2-(5-Methyl-4-imidazolylmethylthio)ethylamino]-5-(2-chlorobenzyl)-4-pyrimidone dihydrochloride (i) Ethyl 3-(2-chlorophenyl)propionate (48.4 g) was converted into 5-(2-chlorobenzyl)-2-thiouracil m.p. 223°–224° (ex methanol by the procedure described in Example 4(i).

(ii) 5-(2-Chlorobenzyl)-2-thiouracil (5.05 g) was converted into 5-(2-chlorobenzyl)-2-methylthio-4-pyrimidone, m.p. 171°–173° C. (ex ethanol) by the procedure of Example 1(i). 5-(2-Chlorobenzyl)-2-methylthio-4-pyrimidone (1.6 g) was reacted with 2-(5-methyl-4-imidazolylmethylthio)ethylamine (1.03 g) as described in Example 1(ii), to give a residue, which on treatment with dilute ethanolic hydrogen chloride, gave 2-[2-(5-methyl-4-imidazolylmethylthio)ethylamino]-5-(2-chlorobenzyl)-4-pyrimidone dihydrochloride, m.p. 215°–219° (ex methanol-ethanol).

(Found: C, 46.7; H, 4.9; N, 14.9; S, 6.8; Cl, 22.4; $C_{18}H_{22}Cl_3N_5OS$ requires: C, 46.7; H, 4.8; N, 15.1; S, 6.4; Cl, 23.0%).

EXAMPLE 14

2-[2-(5-Methyl-4-imidazolylmethylthio)ethylamino]-5-(4-phenylbutyl)-4-pyrimidone dihydrochloride (i) Ethyl 6-phenylhexanoate (43.5 g) was converted to 5-(4-phenylbutyl)-2-thiouracil, m.p. 177.5°–181° (ex ethanol-water), as described in Example 4(i).

(ii) 5-(4-Phenylbutyl)-2-thiouracil (3.05 g) was converted into 5-(4-phenylbutyl)-2-methylthio-4-pyrimidone m.p. 146°–149° (ex ethanol), by the procedure of Example 1(i). 5-(4-Phenylbutyl)-2-methylthio-4-pyrimidone (1.89 g) was reacted with 2-(5-methyl-4-imidazolylmethylthio)ethylamine (1.18 g) as described in Example 1(ii) to give a residue, which on treatment with dilute ethanolic hydrogen chloride, gave 2-[2-(5-methyl-4-imidazolylmethylthio)ethylamino]-5-(4-phenylbutyl)-4-pyrimidone dihydrochloride, m.p. 207°–209.5° (ex ethanol)

(Found: C, 53.3; H, 6.2; N, 14.8; S, 6.8; Cl, 14.8. $C_{21}H_{29}Cl_2N_5OS$ requires: C, 53.6; H, 6.2; N, 14.9; S, 6.8; Cl, 15.1%).

EXAMPLE 15

2-[2-(5-Methyl-4-imidazolylmethylthio)ethylamino]-5-(5-(1,3-benzodioxolyl)methyl)-4-pyrimidone dihydrochloride (i) Ethyl 3-(5-(1,3-benzodioxolyl)propionate (17.5 g) was converted into 5-(1,3-benzodioxolyl)methyl)-2-thiouracil m.p. 158°–159° (ex ethanol/methanol, 1:1), by the procedure described in Example 4(i).

(ii) 5-(5-(1,3-Benzodioxolyl)methyl)-2-thiouracil (2.9 g) was converted into 5-(5-(1,3-benzodioxolyl)methyl)-2-methylthio-4-pyrimidone, m.p. 197°–198° (ex acetonitrile) by the procedure of Example 1(i).

5-(5-(1,3-Benzodioxolyl)methyl)-2-methylthio-4-pyrimidone (1.2 g) was reacted with 2-(5-methyl-4-imidazolylmethylthio)ethylamine (0.77 g) as described in Example 1(ii), to give a residue, which, on treatment with ethanolic hydrogen chloride, gave the title product m.p. 230°–232° (ex ethanol).

(Found: C, 48.5; H, 5.1; N, 14.5; S, 6.7; Cl, 14.7; $C_{19}H_{23}Cl_2N_5O_3S$ requires: C, 48.3; H, 4.9; N, 14.8; S, 6.8; Cl, 15.0%).

EXAMPLE 16

2-[2-(5-Methyl-4-imidazolylmethylthio)ethylamino]-5-(3ethoxybenzyl)-4-pyrimidone dihydrochloride 5-(3-Ethoxybenzyl)-2-thiouracil (5.0 g) was converted into 5-(3-ethoxybenzyl)-2-methylthio-4-pyrimidone, m.p. 136°–138°. (ex acetonitrile) by the procedure of Example 1(i). 5-(3-Ethoxybenzyl)-2-methylthio-4-pyrimidone (2.0 g) was reacted with 2-(5-methyl-4-imidazolylmethylthio)ethylamine (1.25 g) as described in Example 1(ii), to give a residue which, on treatment with ethanolic hydrogen chloride gave 2-[2-(5-methyl-4-imidazolylmethylthio)ethylamino]-5-(3-ethoxybenzyl)-4-pyrimidone dihydrochloride m.p. 176°–178° (ex ethanol).

(Found: C, 50.6; H, 5.7; N, 14.7; S, 7.1; Cl, 14.7; $C_{20}H_{27}Cl_2N_5O_2S$ requires: C, 50.9; H, 5.8; N, 14.8; S, 6.8; Cl,15.0%).

EXAMPLE 17

2-[2-(5-Methyl-4-imidazolylmethylthio)ethylamino]-5-(3-benzyloxybenzyl)-4-pyrimidone dihydrochloride 5-(3-Benzyloxybbenzyl)-2-thiouracil (4.6 g) was converted into 5-(3-benzyloxybenzyl)-2-methylthio-4-pyrimidone, m.p. 176°–178° (ex ethyl acetate), by the procedure of Example 1(i). 5-(3-Benzyloxybenzyl)-2-methylthio-4-pyrimidone (2.0 g) was reacted with 2-(5-methyl-4-imidazolylmethylthio)ethylamine (1.0 g) as described in Example 1(ii), to give a residue which, on treatment with ethanolic hydrogen chloride gave 2-[2-(5-methyl-4-imidazolylmethylthio)ethylamino]-5-(3-benzyloxybenzyl)-4-pyrimidone dihydrochloride m.p. 193°–194° (ex ethanol/methanol, 1:1).

Found: C, 55.7; H, 5.4; N, 12.9; S, 6.0; Cl, 13.0; $C_{25}H_{29}Cl_2N_5O_2S$ requires; C, 56.2; H, 5.5; N, 13.1; S, 6.0; Cl, 13.3%).

EXAMPLE 18

2-[2-(5-Methyl-4-imidazolylmethylthio)ethylamino]-5-(1-naphthylmethyl)-4-pyrimidone dihydrochloride 5-(1-Naphthylmethyl)-2-thiouracil (6.7 g) was converted into 5-(1-naphthylmethyl)-2-methylthio-4-pyrimidone, m.p. 178°–180° (ex methanol) by the procedure of Example 1(i). 5-(1-Naphthylmethyl)-2-methylthio-4-pyrimidone (0.4 g) was reacted with 2-(5-methyl-4-imidazolylmethylthio)ethylamine (0.25 g) as described in Example 1(ii), to give a residue which, on treatment with ethanolic hydrogen chloride gave 2-[2-(5-methyl-4-imidazolylmethylthio)ethylamino]-5-(1-naphthylmethyl)-4-pyrimidone dihydrochloride, m.p. 228°–230° (ex ethanol).

(Found: C, 55.0; H, 5.3; N, 14.4; S, 6.6; Cl, 14.5; $C_{22}H_{25}ClN_5OS$ requires: C, 55.2; H, 5.3; N, 14.6; S, 6.7; Cl, 14.8%).

EXAMPLE 19

(i) Ethyl 3-(3,4,5-trimethoxyphenyl)propionate (82.4 g) was converted into 5-(3,4,5-trimethoxybenzyl)-2-thiouracil, m.p. 214°–215° C. (ex ethanol) by the procedure of Example 4(i).

(ii) 5-(3,4,5-Trimethoxybenzyl)-2-thiouracil (12.9 g) was converted into 5-(3,4,5-trimethoxybenzyl)-2-methylthio-4-pyrimidone, m.p. 158°–159° C. (ex ethanol) by the procedure of Example 1(i).

(iii) 5-(3,4,5-Trimethoxybenzyl)-2-methylthio-4-pyrimidone (2.39 g) was reacted with 2-(5-methyl-4-imidazolylmethylthio)ethylamine (1.37 g) by the procedure of Example 3 to give 2-[2-(5-methyl-4-imidazolylmethylthio)-ethylamino]-5-(3,4,5-trimethoxybenzyl)-4-pyrimidone dihydrochloride, m.p. 170°–174° C. (ex ethanol).

Found: C, 48.5; H, 5.7, H, 13.5; S, 5.9; Cl, 13.7; $C_{21}H_{29}Cl_2N_5O_4S$ requires: C, 48.7; H, 5.6; N, 13.5 S, 6.2; Cl, 13.7%).

EXAMPLE 20

2-[2-(5-Methyl-4-imidazolylmethylthio)ethylamino]-5-(4-methoxybenzyl)-4-pyrimidone (1.5 g) was dissolved in pyridine (35 ml) and refluxed with phosphorus pentasulphide (0.87 g) for 7 hours. The pyridine was evaporated and the residue washed with boiling water. The residue was treated with 2NHCl and recrystallised to give 2-[2-(5-methyl-4-imidazolylmethylthio)ethylamino]-5-(4-methoxybenzyl)pyrimid-4-thione dihydrochloride m.p. 202°–206° C. (ex 2N HCl)

(Found: C, 47.6; H, 5.3; N, 14.6; S, 13.2; Cl, 15.5 $C_{19}H_{25}N_5OS_2$ requires: C, 48.1; H, 5.3; N, 14.8; S, 13.5; Cl, 15.0%).

EXAMPLE 21

Substitution of:
(a) 2-(2-imidazolylmethylthio)ethylamine
(b) 2-(4-imidazolylmethylthio)ethylamine
(c) 2-(5-bromo-4-imidazolylmethylthio)ethylamine
(d) 2-(5-trifluoromethyl-4-imidazolylmethylthio)ethylamine
(e) 2-(5-hydroxymethyl-4-imidazolylmethylthio)ethylamine
(f) 2-(2-pyridylmethylthio)ethylamine
(g) 2-(3-methyl-2-pyridylmethylthio)ethylamine
(h) 2-(3-methoxy-2-pyridylmethylthio)ethylamine
(i) 2-(3-chloro-2-pyridylmethylthio)ethylamine
(j) 2-(3-amino-2-pyridylmethylthio)ethylamine
(k) 2-(3-hydroxy-2-pyridylmethylthio)ethylamine
(l) 2-(3-isothiazolylmethylthio)ethylamine
(m) 2-(4-bromo-3-isothiazolylmethylthio)ethylamine
(n) 2-(3-(1,2,5)-thiadiazolylmethylthio)ethylamine
(o) 2-(4-chloro-3-(1,2,5)-thiadiazolylmethylthio)ethylamine
(p) 2-(5-amino-2-(1,3,4)-thiadiazolylmethylthio)ethylamine
(q) 2-(2-thiazolylmethylthio)ethylamine for 2-(5-methyl-4-imidazolylmethylthio)ethylamine in the procedure of Example 7 leads to the production of:
(a) 2-[2-(2-imidazolylmethylthio)ethylamino]-5-(4-methoxybenzyl)-4-pyrimidone
(b) 2-[2-(4-imidazolylmethylthio)ethylamino]-5-(4-methoxybenzyl)-4-pyrimidone
(c) 2-[2-(5-bromo-4-imidazolylmethylthio)ethylamino]-5-(4-methoxybenzyl)-4-pyrimidone
(d) 2-[2-(5-trifluoromethyl-4-imidazolylmethylthio)ethylamino]-5-(4-methoxybenzyl)-4-pyrimidone
(e) 2-[2-(5-hydroxymethyl-4-imidazolylmethylthio)ethylamino]-5-(4-methoxybenzyl)-4-pyrimidone
(f) 2-[2-(2-pyridylmethylthio)ethylamino]-5-(4-methoxybenzyl)-4-pyrimidone
(g) 2-[2-(3-methyl-2-pyridylmethylthio)ethylamino]-5-(4-methoxybenzyl)-4-pyrimidone
(h) 2-[2-(3-methoxy-2-pyridylmethylthio)ethylamino]-5-(4-methoxybenzyl)-4-pyrimidone
(i) 2-[2-(3-chloro-2-pyridylmethylthio)ethylamino]-5-(4-methoxybenzyl)-4-pyrimidone
(j) 2-[2-(3-amino-2-pyridylmethylthio)ethylamino]-5-(4-methoxybenzyl)-4-pyrimidone
(k) 2-[2-(3-hydroxy-2-pyridylmethylthio)ethylamino]-5-(4-methoxybenzyl)-4-pyrimidone
(l) 2-[2-(3-isothiazolylmethylthio)ethylamino]-5-(4-methoxybenzyl)-4-pyrimidone
(m) 2-[2-(4-bromo-3-isothiazolylmethylthio)ethylamino]-5-(4-methoxybenzyl)-4-pyrimidone
(n) 2-[2-(3-(2,5)-thiadiazolylmethylthio)ethylamino]-5-(4-methoxybenzyl)-4-pyrimidone
(o) 2-[2-(4-chloro-3-(1,2,5)-thiadiazolylmethylthio)ethylamino]-5-(4-methoxybenzyl)-4-pyrimidone
(p) 2-[2-(5-amino-2-(1,3,4)-thiadiazolylmethylthio)ethylamino]-5-(4-methoxybenzyl)-4-pyrimidone
(q) 2-[2-(2-thiazolylmethylthio)ethylamino]-5-(4-methoxybenzyl)-4-pyrimidone Substitution of the above listed 4-pyrimidones for 2-[2-(5-methyl-4-imidazolylmethylthio)ethylamino]-5-(4-methoxybenzyl)-4-pyrimidone in the procedure of Example 20 leads to the production of:
(a) 2-[2-(2-imidazolylmethylthio)ethylamino]-5-(4-methoxybenzyl)pyrimid-4-thione
(b) 2-[2-(4-imidazolylmethylthio)ethylamino]-5-(4-methoxybenzyl)pyrimid-4-thione
(c) 2-[2-(5-bromo-4-imidazolylmethylthio)ethylamino]-5-(4-methoxybenzyl)pyrimid-4-thione
(d) 2-[2-(5-trifluoromethyl-4-imidazolylmethylthio)ethylamino]-5-(4-methoxybenzyl)pyrimid-4-thione
(e) 2-[2-(5-hydroxymethyl-4-imidazolylmethylthio)ethylamino]-5-(4-methoxybenzyl)pyrimid-4-thione
(f) 2-[2-(2-pyridylmethylthio)ethylamino]-5-(4-methoxybenzyl)pyrimid-4-thione
(g) 2-[2-(3-methyl-2-pyridylmethylthio)ethylamino]-5-(4-methoxybenzyl)pyrimid-4-thione;
(h) 2-[2-(3-methoxy-2-pyridylmethylthio)ethylamino]-5-(4-methoxybenzyl)pyrimid-4-thione
(i) 2-[2-(3-chloro-2-pyridylmethylthio)ethylamino]-5-(4-methoxybenzyl)pyrimid-4-thione
(j) 2-[2-(3-amino-2-pyridylmethylthio)ethylamino]-5-(4-methoxybenzy)pyrimid-4-thione
(k) 2-[2-(3-hydroxy-2-pyridylmethylthio)ethylamino]-5-(4-methoxybenzyl)pyrimid-4-thione
(l) 2-[2-(3-isothiazolylmethylthio)ethylamino]-5-(4-methoxybenzyl)pyrimid-4-thione
(m) 2-[2-(4-bromo-3-isothiazolylmethylthio)ethylamino]-5-(4-methoxybenzyl)pyrimid-4-thione
(n) 2-[2-(3-(1,2,5)-thiadiazolylmethylthio)ethylamino]-5-(4-methoxybenzyl)pyrimid-4-thione
(o) 2-[2-(4-chloro-3-(1,2,5)-thiadiazolylmethylthio)ethylamino]-5-(4methoxybenzyl)pyrimid-4-thione
(p) 2-[2-(5-amino-2-(1,3,4)-thiadiazolylmethylthio)ethylamino]-5-(4-methoxybenzyl)pyrimid-4-thione
(q) 2-[2-(2-thiazolylmethylthio)ethylamino]-5-(4-methoxybenzyl)pyrimid-4-thione Substitution of the above-listed amines for 2-(5-methyl-4-imidazolylmethylthio)ethylamine in the procedure of Example 2 leads to the production of:

(a) 2-[2-(2-imidazolylmethylthio)ethylamino]-5-(2-phenylethyl)-4-pyrimidone
(b) 2-[2-(4-imidazolylmethylthio)ethylamino]-5-(2-phenylethyl)-4-pyrimidone
(c) 2-[2-(5-bromo-4-imidazolylmethylthio)ethylamino]-5-(2-phenylethyl)-4-pyrimidone
(d) 2-[2-(5-trifluoromethyl-4-imidazolylmethylthio)ethylamino]-5-(2-phenylethyl)-4-pyrimidone;
(e) 2-[2-(5-hydroxymethyl-4-imidazolylmethylthio)ethylamino]-5-(2-phenylethyl)-4-pyrimidone;
(f) 2-[2-(2-pyridylmethylthio)ethylamino]-5-(2-phenylethyl)-4-pyrimidone
(g) 2-[2-(3-methyl-2-pyridylmethylthio)ethylamino]-5-(2-phenylethyl)-4-pyrimidone
(h) 2-[2-(3-methoxy-2-pyridylmethylthio)ethylamino]-5-(2-phenylethyl)-4-pyrimidone
(i) 2-[2-(3-chloro-2-pyridylmethylthio)ethylamino]-5-(2-phenylethyl)-4-pyrimidone
(j) 2-[2-(3-amino-2-pyridylmethylthio)ethylamino]-5-(2-phenylethyl)-4-pyrimidone
(k) 2-[2-(3-hydroxy-2-pyridylmethylthio)ethylamino]-5-(2-phenylethyl)-4-pyrimidone
(l) 2-[2-(3-isothiazolylmethylthio)ethylamino]-5-(2-phenylethyl)-4-pyrimidone
(m) 2-[2-(4-bromo-3-thiazolylmethylthio)ethylamino]-5-(2-phenylethyl)-4-pyrimidone
(n) 2-[2-(3-(1,2,5)-thiadiazolylmethylthio)ethylamino]-5-(2-phenylethyl)-4-pyrimidone
(o) 2-[2-(4-chloro-3-(1,2,5)-thiadiazolylmethylthio)ethylamino]-5-(2-phenylethyl)-4-pyrimidone
(p) 2-[2-(5-amino-2-(1,3,4)-thiadiazolylmethylthio)ethylamino]-5-(2-phenylethyl)-4-pyrimidone
(q) 2-[2-(2-thiazolylmethylthio)ethylamino]-5-(2-phenylethyl)-4-pyrimidone Substitution of the above-listed amines for 2-(5-methyl-4-imidazolylmethylthio)ethylamine in the procedure of Example 11 leads to the production of:
(a) 2-[2-(2-imidazolylmethylthio)ethylamino]-5-benzyloxy-4-pyrimidone
(b) 2-[2-(4-imidazolylmethylthio)ethylamino]-5-benzyloxy-4-pyrimidone
(c) 2-[2-(5-bromo-4-imidazolylmethylthio)ethylamino]-5-benzyloxy-4-pyrimidone
(d) 2-[2-(5-trifluoromethyl-4-imidazolylmethylthio)ethylamino]-5-benzyloxy-4-pyrimidone
(e) 2-[2-(5-hydroxymethyl-4-imidazolylmethylthio)ethylamino]-5-benzyloxy-4-pyrimidone
(f) 2-[2-(2-pyridylmethylthio)ethylamino]-5-benzyloxy-4-pyrimidone
(g) 2-[2-(3-methyl-2-pyridylmethylthio)ethylamino]-5-benzyloxy-4-pyrimidone
(h) 2-[2-(3-methoxy-2-pyridylmethylthio)ethylamino]-5-benzyloxy-4-pyrimidone
(i) 2-[2-(3-chloro-2-pyridylmethylthio)ethylamino]-5-benzyloxy-4-pyrimidone
(j) 2-[2-(3-amino-2-pyridylmethylthio)ethylamino]-5-benzyloxy-4-pyrimidone
(k) 2-[2-(3-hydroxy-2-pyridylmethylthio)ethylamino]-5-benzyloxy-4-pyrimidone
(l) 2-[2-(3-isothiazolylmethylthio)ethylamino]-5-benzyloxy-4-pyrimidone
(m) 2-[2-(4-bromo-3-isothiazolylmethylthio)ethylamino]-5-benzyloxy-4-pyrimidone
(n) 2-[2-(3-(1,2,5)-thiadiazolylmethylthio)ethylamino]-5-benzyloxy-4-pyrimidone
(o) 2-[2-(4-chloro-3-(1,2,5)-thiadiazolylmethylthio)ethylamino]-5-benzoyloxy-4-pyrimidone
(p) 2-[2-(5-amino-2-(1,3,4)-thiadiazolylmethylthio)ethylamino]-5-benzyloxy-4-pyrimidone
(q) 2-[2-(2-thiazolylmethylthio)ethylamino]-5-benzyloxy-4-pyrimidone Substitution of the above-listed amines for 2-(5-methyl-4-imidazolylmethylthio)ethylamine in the procedure of Example 12 leads to the production of:
(a) 2-[2-(2-imidazolylmethylthio)ethylamino]-5-(3-methoxybenzyl)-4-pyrimidone
(b) 2-[2-(4-imidazolylmethylthio)ethylamino]-5-(3-methoxybenzyl)-4-pyrimidone
(c) 2-[2-(5-bromo-4-imidazolylmethylthio)ethylamino]-5-(3-methoxybenzyl)-4-pyrimidone
(d) 2-[2-(5-trifluoromethyl-4-imidazolylmethylthio)ethylamino-5-(3-methoxybenzyl)-4-pyrimidone
(e) 2-[2-(5-hydroxymethyl-4-imidazolylmethylthio)ethylamino]-5-(3-methoxybenzyl)-4-pyrimidone
(f) 2-[2-(2-pyridylmethylthio)ethylamino]-5-(3-methoxybenzyl)-4-pyrimidone
(g) 2-[2-(3-methyl-2-pyridylmethylthio)ethylamino]-5-(3-methoxybenzyl)-4-pyrimidone
(h) 2-[2-(3-methoxy-2-pyridylmethylthio)ethylamino]-5-(3-methoxybenzyl)-4-pyrimidone
(i) 2-[2-(3-chloro-2-pyridylmethylthio)ethylamino]-5-(3-methoxybenzyl)-4-pyrimidone
(j) 2-[2-(3-amino-2-pyridylmethylthio)ethylamino]-5-(3-methoxybenzyl)-4-pyrimidone
(k) 2-[2-(3-hydroxy-2-pyridylmethylthio)ethylamino]-5-(3-methoxybenzyl)-4-pyrimidone
(l) 2-[2-(3-isothiazolylmethylthio)ethylamino]-5-(3-methoxybenzyl)-4-pyrimidone
(m) 2-[2-(4-bromo-3-isothiazolylmethylthio)ethylamino]-5-(3-methoxybenzyl)-4-pyrimidone
(n) 2-[2-(3-(1,2,5)-thiadiazolylmethylthio)ethylamino]-5-(3-methoxybenzyl)-4-pyrimidone
(o) 2-[2-(4-chloro-3-(1,2,5)-thiadiazolylmethylthio)ethylamino]-5-(3-methoxybenzyl)-4-pyrimidone
(p) 2-[2-(5-amino-2-(1,3,4)-thiadiazolylmethylthio)ethylamino]-5-(3-methoxybenzyl)-4-pyrimidone
(q) 2-[2-(2-thiazolylmethylthio)ethylamino]-5-(3-methoxybenzyl)-4-pyrimidone 2-(4-chloro-3-(1,2,5)-thiadiazolylmethylthio)ethylamine may be prepared by the following route: 3-Methyl(1,2,5)thiadiazole is chlorinated for 4 days in acetonitrile at 25° to give 4-chloro-3-methyl(1,2,5)-thiadiazole (oil) which is treated with N-bromosuccinimide in carbon tetrachloride to give 3-bromomethyl-4-chloro(1,2,5)thiadiazole (oil), the 100 MHz n.m.r. in CDCl$_3$ had singlet at 4.66δ. 3-Bromomethyl-4-chloro(1,2,5)thiadiazole was treated with cysteamine and sodium ethoxide in ethanol to give 2-(4-chloro-3(1,2,5)thiadiazolylmethylthio)ethylamine (oil). A 60 MHz n.m.r. spectrum (CDCl$_3$) gave a singlet at 3.91 attributed to the Het-CH$_2$-S protons.

EXAMPLE 22

Substitution of 4-(4-imidazolyl)butylamine for 2-(5-methyl-4-imidazolylmethylthio)ethylamine in the procedure of Example 12 leads to the production of 2-[4-(4-imidazolyl)butylamino]-5-(3-methoxybenzyl)-4-pyrimidone, m.p. 193°-194°.

EXAMPLE 23

Treatment of ethyl butyroacetate with sodium ethoxide and 4-methoxybenzyl chloride gives ethyl α-(4-methoxybenzyl)butyroacetate which is refluxed with thiourea and sodium ethoxide to give 5-(4-methoxybenzyl)-6-propyl-2-thiouracil. Substitution of 5-(4-methoxybenzyl)-6-Propyl-2-thiouracil for 5-(4-chlorobenzyl)-2-thiouracil in the general procedure of Example 1 gives 5-(4-methoxybenzyl)-2-methylthio-6-propyl-4-pyrimidone and 2-[2-(5-methyl-4-imidazolylmethylthio)ethylamino]-5-(4-methoxybenzyl)-6-propyl-4-pyrimidone.

EXAMPLE 24

Substitution of
(a) ethyl 3-(2-naphthyl)propionate
(b) ethyl 3-(4-trifluoromethylphenyl)propionate
(c) ethyl 3-(4-dimethylaminophenyl)propionate
(d) ethyl 3-(4-phenoxyphenyl)propionate
(e) ethyl 3-(4-(4-chlorophenoxy)phenyl)propionate
(f) ethyl 3-(4-(4-methoxyphenoxy)phenylpropionate
(g) ethyl 3-(4-biphenylyl)propionate
(h) ethyl 3-(4'-chloro-4-biphenylyl)propionate
(i) ethyl 3-(4'-methoxy-4-biphenylyl)propionate
for ethyl 3-(3-chlorophenyl)propionate in the procedure of Example 4 leads to the production of:
(a) 5-(2-naphthylmethyl)-2-methylthio-4-pyrimidone
(b) 5-(4-trifluoromethylbenzyl)-2-methylthio-4-pyrimidone (c) 5-(4-dimethylaminobenzyl)-2-methylthio-4-pyrimidone
(d) 5-(4-phenoxybenzyl)-2-methylthio-4-pyrimidone
(e) 5-(4-(4-chlorophenoxy)benzyl)-2-methylthio-4-pyrimidone
(f) 5-(4-(4-methoxyphenoxy)benzyl)-2-methylthio-4-pyrimidone
(g) 5-(4-phenylbenzyl)-2-methylthio-4-pyrimidone
(h) 5-(4-(4-chlorophenyl)benzyl)-2-methylthio-4-pyrimidone
(i) 5-(4-(4-methoxyphenyl)benzyl)-2-methylthio-4-pyrimidone
and
(a) 2-[2-(5-methyl-4-imidazolylmethylthio)ethylamino]-5-(2-naphthylmethyl)-4-pyrimidone
(b) 2-[2-(5-methyl-4-imidazolylmethylthio)ethylamino]-5-(4-trifluoromethylbenzyl)-4-pyrimidone
(c) 2-[2-(5-methyl-4-imidazolylmethylthio)ethylamino]-5-(4-dimethylaminobenzyl)-4-pyrimidone
(d) 2-[2-(5-methyl-4-imidazolylmethylthio)ethylamino]-5-(4-phenoxybenzyl)-4-pyrimidone
(e) 2-[2-(5-methyl-4-imidazolylmethylthio)ethylamino]-5-(4-(4-chlorophenoxy)benzyl)-4-pyrimidone
(f) 2-[2-(5-methyl-4-imidazolylmethylthio)ethylamino]-5-(4-(4-methoxyphenoxy)benzyl)-4-pyrimidone
(g) 2-[2-(5-methyl-4-imidazolylmethylthio)ethylamino]-5-(4-phenylbenzyl)-4-pyrimidone
(h) 2-[2-(5-methyl-4-imidazolylmethylthio)ethylamino]-5-4-(4-chlorophenyl)benzyl)-4-pyrimidone
(i) 2-[2-(5-methyl-4-imidazolylmethylthio)ethylamino]-5-4-(4-methoxyphenyl)benzyl))-4-pyrimidone

EXAMPLE 25

Treatment of 2-[2-(5-methyl-4-imidazolylmethylthio)ethylamino]-5-(3-benzyloxybenzyl)-4-pyrimidone with hydrogen bromide in acetic acid leads to the production of 2-[2-(5-methyl-4-imidazolylmethylthio)ethylamino]-5-(3-hydroxybenzyl)-4-pyrimidone.

EXAMPLE 26

(a) Butyrolactone is treated with sodium and ethyl formate, and the product is successively treated with thiourea and methyl iodide to give 5-(2-hydroxyethyl)-2-methylthio-4-pyrimidone.

(b) 5-(2-Hydroxyethyl)-2-methylthio-4-pyrimidone is treated with thionyl chloride and the product is reacted with the sodium derivative of (1) 4-methoxybenzyl alcohol and (2) 4-methoxybenzyl mercaptan, to give:
1. 5-(2-(4-methoxybenzyloxy)ethyl)-2-methylthio-4-pyrimidone
2. 5-(2-(4-methoxybenzylthio)ethyl)-2-methylthio-4-pyrimidone
(c) substitution of:
1. 5-(2-(4-methoxybenzyloxy)ethyl)-2-methylthio-4-pyrimidone
2. 5-(2-(4-methoxybenzylthio)ethyl)-2-methylthio-4-pyrimidone for 5-(4-chlorobenzyl)-2-methylthio-4-pyrimidone in the general procedure of Example 1(ii) leads to the production of:
1. 2-[2-(5-methyl-4-imidazolylmethylthio)ethylamino]-5-(2-(4-methoxybenzyloxy)ethyl)-4-pyrimidone
2. 2-[2-(5-methyl-4-imidazolylmethylthio)ethylamino]-5-(2-(4-methoxybenzylthio)ethyl)-4-pyrimidone
(d) substitution of (1) phenol and (2) thiophenol for p-methoxybenzyl alcohol in procedure (bii) and (c) above leads to the production of:
1. 2-[2-(5-methyl-4-imidazolylmethylthio)ethylamino]-5-(2-phenoxyethyl)-4-pyrimidone
2. 2-[2-(5-methyl-4-imidazolylmethylthio)ethylamino]-5-(2-phenylthioethyl)-4-pyrimidone
(e) substitution of (1) 2-phenylethanol and (2) 2-phenylethyl mercaptan for p-methoxybenzyl alcohol in procedure (bii) and (c) above leads to the production of
1. 2-[2-(5-methyl-4-imidazolylmethylthio)ethylamino]-5-(2-(2-phenylethoxy)ethyl)-4-pyrimidone
2. 2-[2-(5-methyl-4-imidazolylmethylthio)ethylamino]-5-(2-(2-phenylethylthio)ethyl-4-pyrimidone
(f) substitution of caprolactone for butyrolactone in procedure (a) (bii) and (c) above leads to the production of
1. 2-[2-(5-methyl-4-imidazolylmethylthio)ethylamino]-5-(3-(4-methoxybenzyloxy)propyl)-4-pyrimidone
2. 2-[2-(5-methyl-4-imidazolylmethylthio)ethylamino]-5-(3-(4-methoxybenzylthio)propyl)-4-pyrimidone.

EXAMPLE 27

Substitution of
(a) ethyl 3-phenylpropoxyacetate
(b) ethyl 3-phenylpropylthioglycolate for ethyl benzyloxyacetate in the procedure of Example 11 results in the preparation of:
(a) 5-(5-(3-phenylpropoxy)-2-methylthio-4-pyrimidone
(b) 5-(3-phenylpropylthio)-2-methylthio-4-pyrimidone
and
(a) 2-[2-(5-methyl-4-imidazolylmethylthio)ethylamino]-5-(3-phenylpropoxy)-4-pyrimidone
(b) 2-[2-(5-methyl-4-imidazolylmethylthio)ethylamino]-5-(3-phenylpropylthio)-4-pyrimidone.

EXAMPLE 28

Substitution of
(a) 5-[3-(2-(4-methoxyphenyl)ethoxy)benzyl]-2-thiouracil
(b) 5-[3-(3-chlorobenzyloxy)benzyl]-2-thiouracil for 5-(3-benzyloxybenzyl)-2-thiouracil in the general procedure of Example 17 leads to the production of:
(a) 5-[3-(2-(4-methoxyphenyl)ethoxy)benzyl]-2-methylthio-4-pyrimidone
(b) 5-[3-(3-chlorobenzyloxy)benzyl]-2-methylthio-4-pyrimidone
and (a) 2-[2-(5-methyl-4-imidazolylmethylthio)ethylamino]-5-[3-(2-(4-methoxyphenyl)ethoxy)benzyl]-4-pyrimidone
(b) 2-[2-(5-methyl-4-imidazolylmethylthio)ethylamino]-5-[3-(3-chlorobenzyloxy)benzyl]-4-pyrimidone.

EXAMPLE 29

Substitution of ethyl 3-(3-bromophenyl)propionate for ethyl 3-(3-chlorophenyl)propionate in the procedure of Example 4 leads to the production of:
5-(3-bromobenzyl)-2-methylthio-4-pyrimidone and
2-[2-(5-methyl-4-imidazolylmethylthio)ethylamino]-5-(3-bromobenzyl)-4-pyrimidone

EXAMPLE 30

Treatment of ethyl 3-(3-hydroxyphenyl)propionate with dimethoxymethane and substitution of the product for ethyl 3-(3-chlorophenyl)propionate in the procedure of Example 4 leads to the production of 5-[3-(methoxymethoxy)benzyl]-2-methylthio-4-pyrimidone and 2-[2-(5-methyl-4-imidazolylmethylthio)ethylamino]-5-[3-(methoxymethoxy)benzyl]-4-pyrimidone. Treatment of this product with hydrochloric acid gives 2-[2-(5-methyl-4-imidazolylmethylthio)ethylamino]-5-(3-hydroxybenzyl)-4-pyrimidone.

EXAMPLE 31

| Pharmaceutical composition:- Ingredients | Amounts |
| --- | --- |
| 2-[2-(5-methyl-4-imidazolylmethylthio)-ethylamino]-5-(3-methoxybenzyl)-4-pyrimidone dihydrochloride | 75 mg |
| Sucrose | 75 mg |
| Starch | 25 mg |
| Talc | 5 mg |
| Stearic Acid | 2 mg |

The ingredients are screened, mixed and filled into a hard gelatin capsule.

EXAMPLE 32

| Pharmaceutical composition:- Ingredients | Amounts |
| --- | --- |
| 2-[2-(5-methyl-4-imidazolylmethylthio)-ethylamino]-5-(3-methoxybenzyl)-4-pyrimidone dihydrochloride | 100 mg |
| Lactose | 100 mg |

The ingredients are screened, mixed and filled into a hard gelatin capsule.

Similarly, the other compounds of Formula 3 may be formulated into pharmaceutical compositions by the procedures of Examples 31 and 32.

The pharmaceutical compositions prepared as in the foregoing examples are administered to a subject within the dose ranges given hereabove to block histamine $H_1$- and $H_2$-receptors.

EXAMPLE 33

(i) Ethyl 3-(2-methoxyphenyl)propionate (65.0 g) was converted into 5-(2-methoxybenzyl)-2-thiouracil, m.p. 192°–193° C. (ex. ethanol/H$_2$O, 1:1) by the procedure of Example 4(i).

(ii) 5-(2-Methoxybenzyl)-2-thiouracil (9.0 g) was converted into 5-(2-methoxybenzyl)-2-methylthio-4-pyrimidone, m.p. 163°–166° C. (ex. ethanol) by the procedure of Example 1(i).

(iii) 5-(2-Methoxybenzyl)-2-methylthio-4-pyrimidone (2.00 g) was reacted with 2-(5-methyl-4-imidazolylmethylthio)-ethylamine (1.37 g) by the procedure of Example 1(ii) to give 2-[2-(5-methyl-4-imidazolylmethylthio)ethylamino]-5-(2-methoxybenzyl)-4-pyrimidone, m.p. 163°–167° C. (ex ethanol).

(Found: C, 58.4; H, 6.1; N, 17.6; S, 8.2; $C_{19}H_{23}N_5O_2S$ requires: C, 59.2; H, 6.0; N, 18.2; S, 8.3%).

EXAMPLE 34

(i) Ethyl 3-(3,4-dimethoxyphenyl)propionate (37.5 g) was converted into 5-(3,4-dimethoxybenzyl)-2-thiouracil, m.p. 236°–237° C. (ex ethanol) by the procedure of Example 4(i).

(ii) 5-(3,4-Dimethoxybenzyl)-2-thiouracil (7.3 g) was converted to 5-(3,4-dimethoxybenzyl)-2-methylthio-4-pyrimidone, m.p. 199°–200° C. (ex ethanol) by the procedure of Example 1(i).

(iii) 5-(3,4-Dimethoxybenzyl)-2-methylthio-4-pyrimidone (1.3 g) was reacted with 2-(5-methyl-4-imidazolylmethylthio)ethylamine (0.76 g) by the procedure of Example 3 to give 2-[2-(5-methyl-4-imidazolylmethylthio)ethylamino]-5-(3,4-dimethoxybenzyl)-4-pyrimidone dihydrochloride, m.p. 226°–230° C., (ex methanol).

(Found: C, 48.1; H, 5.5; N, 14.0; S, 6.5: Cl, 14.2; $C_{20}H_{27}Cl_2N_5O_3S$; requires: C, 49.2; H, 5.6; N, 14.3; S, 6.6; Cl, 14.5%).

EXAMPLE 35

(i) Ethyl 3-(3-trifluoromethylphenyl)propionate (90.0 g) was converted to 5-(3-trifluoromethylbenzyl)-2-thiouracil, m.p. 217°–219° C. (ex ethanol/methanol) by the procedure of Example 4 (i).

(ii) 5-(3-trifluoromethylbenzyl)-2-thiouracil (40.13 g) was converted into 5-(3-trifluoromethylbenzyl)-2-methylthio-4-pyrimidone, m.p. 187°–189° C. (ex ethanol) by the procedure of Example 1(i).

(iii) 5-(3-trifluoromethylbenzyl)-2-methylthio-4-pyrimidone (2.5 g) was reacted with 2-(5-methyl-4-imidazolylmethylthio)ethylamine (1.43 g) by the procedure of Example 3 to give 2-[2-(5-methyl-4-imidazolylmethylthio)ethylamino]-5-(3-trifluoromethylbenzyl)-4-pyrimidone dihydrochloride, m.p. 174°–176° C. (ex Propan-2-ol)

(Found: C, 45.8; H, 4.4: N, 14.0: S, 6.6; Cl, 13.9; $C_{19}H_{22}Cl_2F_3N_5OS$; requires: C, 46.0; H, 4.5; N, 14.1; S, 6.5; Cl, 14.3%).

EXAMPLE 36

2-[2-(5-Methyl-4-imidazolylmethylthio)ethylamino]-5-(3-methoxybenzyl)-4-pyrimidone (2.35 g) was suspended in dry dichloromethane (30 ml) and boron tribromide (6.49 g) carefully added. The mixture was stirred in a dry atmosphere overnight. Careful addition of water (30 ml) was followed by separation of the two phases. The aqueous phase was treated in NaHCO$_3$ which precipitated a tacky solid which was repeatedly washed with water until it became solid, when it was filtered and dried. Treatment with ethanolic HCl gave 2-[2-(5-methyl-4-imidazolylmethylthio)ethylamino]-5-(3-hydroxybenzyl)-4-pyrimidone dihydrochloride, m.p. 142°–144° (ex. ethanol)

(Found: C, 48.5; H, 5.2; N, 15.7; S, 7.3; Cl, 15.8: $C_{18}H_{23}Cl_2N_5O_2S$ requires: C, 48.7; H, 5.2; N, 15.8; S, 7.2; Cl, 16.0%).

EXAMPLE 37

2-[2-(5-Methyl-4-imidazolylmethylthio)ethylamino]-5-(4-methoxybenzyl)-4-pyrimidone (5.66 g) was reacted with boron tribromide (14.73 g) using the procedure of Example 36 to give 2-[2-(5-methyl-4-imidazolylmethylthio)ethylamino]-5-(4-hydroxybenzyl)-4-pyrimidone dihydrochloride, m.p. 207°–210° C. (ex ethanol)

(Found: C, 48.4; H, 5.1 N, 15.5; S, 7.2; Cl, 15.4 $C_{18}H_{23}Cl_2N_5O_2S$ requires: C, 48.7; H, 5.2; N, 15.8; S, 7.2; Cl, 16.0%).

EXAMPLE 38

(a) Ethyl 3-(6-(2,3-dihydro-1,4-benzodioxinyl))propionate was prepared by esterifying 3-(6-(2,3-dihydro-1,4-benzodioxinyl)-prop-2-enoic acid with ethanol in the presence of toluene and sulphuric acid, and hydrogenating the product using palladium-on-charcoal catalyst.

(b) Ethyl 3-(6-(2,3-dihydro-1,4-benzodioxinyl))propionate was converted into 5-(6-(2,3-dihydro-1,4-benzodioxinyl)methyl)-2-thiouracil, m.p. 294°–296° (ex 2-methoxyethanol/ethanol, 2:1) by the procedure of Example 4(i), and the latter compound was converted into 5-(6-(2,3-dihydro-1,4-benzodioxinyl)methyl)-2-methylthio-4-pyrimidone, m.p. 200°–201° C. (ex methanol) by the procedure of Example 1(i).

(c) 5-(6-(2,3-dihydro-1,4-benzodioxinyl)methyl)-2-methylthio-4-pyrimidone (1.50 g) was reacted with 2-(5-methyl-4-imidazolylmethylthio)ethylamine (0.94 g) by the procedure of Example 3 to give 2-[2-(5-methyl-4-imidazolylmethylthio)ethylamino]-5-[6-(2,3-dihydro-1,4-benzodioxinyl)methyl]-4-pyrimidone which was dissolved in dilute hydrobromic acid to give the dihydrobromide, m.p. 210°–214° C. (ex ethanol)

(Found: C, 41.9; H, 4.4; N, 11.9; S, 5.3; Br$^-$, 27.5 $C_{20}H_{25}Br_2N_5O_3S$ requires: C, 41.8; H, 4.4; N, 12.2; S, 5.6; Br$^-$, 27.8%).

EXAMPLE 39

5-(3-Methoxybenzyl )-2-methylthio-4-pyrimidone (2.79 g) was reacted with 2-(2-thiazolylmethylthio)ethylamine (1.86 g) by the procedure of Example 6 to give 2-[2-(2-thiazolylmethylthio)ethylamino]-5-(3-methoxybenzyl)-4-pyrimidone hemihydrochloride m.p. 104°–106° C. (ex Propan-2-ol)

(Found: C, 52.9; N, 13.6; S, 15.5; Cl, 4.6; $C_{18}H_{20}N_4O_2S_2 \cdot \frac{1}{2}$ HCl requires: C, 53.2; H, 5.1; N, 13.8; S, 15.8; Cl, 4.4%).

EXAMPLE 40

3-Fluoro-2-methyl-4-nitropyridine N-oxide is treated with an excess of sodium methoxide and the product is heated in acetic anhydride and deacetylated to give 2-hydroxymethyl-3,4-dimethoxypyridine. 2-Hydroxymethyl-3,4-dimethoxypyridine is treated with thionyl chloride and the product is treated was cysteamine to give 2-(3,4-dimethoxy-2-pyridylmethylthio)ethylamine.

(3) Substitution of 2-(3,4-dimethoxy-2-pyridylmethylthio)ethylamine for 2-(5-methyl-4-imidazolylmethylthio)ethylamine in the procedure of Example 7 leads to the production of 2-[2-(3,4-dimethoxy-2-pyridylmethylthio)ethylamino]-5-(4-methoxybenzyl)-4-pyrimidone.

EXAMPLE 41

(i) 4-Nitro-3-methoxy-2-methylpyridine N-oxide is heated in acetic anhydride and the purified product is deacetylated and reduced with hydrogen and palladium on charcoal to give 4-amino-2-hydroxymethyl-3-methoxypyridine.

(ii) 4-Amino-2-hydroxymethyl-3-methoxypyridine is diazotised in dilute sulphuric acid with sodium nitrite and the diazonium compound is warmed to give 4-hydroxy-2-hydroxymethyl-3-methoxypyridine which may be demethylated with hydrobromic acid.

(iii) Alkylation of 3,4-dihydroxy-2-hydroxymethylpyridine with pelleted sodium hydroxide and
(a) Dibromomethane
(b) 1,2-Dibromoethane
(c) 1,4-Dibromobutane leads to the production of
(a) 4-hydroxymethyl (1,3-dioxolo[4,5-c] pyridine)
(b) 2,3-Dihydro-5-hydroxymethyl-(p-dioxino[2,3-c]pyridine)
(c) 2,3,4,5-Tetrahydro-7-hydroxymethyl-(1,4-dioxocino[2,3-c]-pyrdine)

which may be converted into
(a) 2-[2-(4-(1,3-dioxolo[4,5-c]pyridyl)methylthio)ethylamino]-5-(4-methoxybenzyl)-4-pyrimidone.
(b) 2-[2-(5-(2,3-dihydro-p-dioxino[2,3-c]pyridyl)methylthio)ethylamino]-5-(4-methoxybenzyl)-4-pyrimidone.
(c) 2-[2-(7-(2,3,4,5-tetrahydro-1,4-dioxocino[2,3-c]pyridyl)methylthio)ethylamino]-5-(4-methoxybenzyl)-4-pyrimidone, by successive treatment with thionyl chloride and cysteamine and substitution of the resultant amine for 2-(5-methyl-5-imidazolylmethylthio)ethylamine in the procedure of Example 7.

EXAMPLE 42

Treatment of
(a) 1-hydroxymethylisoquinoline
(b) 5,6,7,8-tetrahydro-1-hydroxymethylisoquinoline with cysteamine in hydrogen bromide gives
(a) 2-(1-isoquinolylmethylthio)ethylamine
(b) 2-(5,6,7,8-tetrahydro-1-isoquinolylmethylthio)ethylamine which, when substituted for 2-(5-methyl-4-imidazolylmethylthio)ethylamine in the procedure of Example 7 gives:
(a) 2-[2-(1-isoquinolylmethylthio)ethylamino]-5-(4-methoxybenzyl)-4-pyrimidone
(b) 2-[2-(1-(5,6,7,8-tetrahydroisoquinolyl)methylthio)ethylamino]-5-(4-methoxybenzyl)-4-pyrimidone.

EXAMPLE 43

Alkylation of
(a) 5-(3-methoxybenzyl)-2-thiouracil
(b) 5-(5-(1,3-benzodioxolyl)methyl)-2-thiouracil
(c) 5-(6-(2,3-dihydro-1,4-benzodioxinyl)-methyl)-2-thiouracil with benzyl chloride and sodium hydroxide gives
(a) 5-(3-methoxybenzyl)-2-benzylthio-4-pyrimidone
(b) 5-(5-(1,3-benzodioxolyl)methyl)-2-benzylthio-4-pyrimidone
(c) 5-(6-(2,3-dihydro-1,4-benzodioxinyl)methyl)-2-benzylthio-4-pyrimidone

What is claimed is:
1. A compound of the formula:

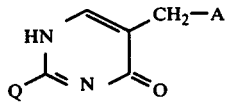
in which Q is loweralkylthio or benzylthio and A is a 1,3-benzodioxolyl or a 2,3-dihydro-1,4-benzodioxinyl ring.
2. A chemical intermediate of claim 1, said intermediate being 5-(5-(1,4-benzodioxolyl)methyl)-2-methylthio-4-pyrimidone.
3. A chemical intermediate of claim 1, said intermediate being 5-(6-(2,3-dihydro-1,4-benzodioxinyl)methyl)-2-methylthio-4-pyrimidone.
* * * * *

UNITED STATES PATENT AND TRADEMARK OFFICE
CERTIFICATE OF CORRECTION

PATENT NO. : 4,145,546
DATED : March 20, 1979
INVENTOR(S) : Thomas H. Brown, Graham J. Durant, John C. Emmett and Charon R. Ganellin It is certified that error appears in the above-identified patent and that said Letters Patent are hereby corrected as shown below:

On the first page of the patent, in the left-hand column, following item [22] insert the following:

[30]   Foreign Application Priority Data

October 2, 1975   United Kingdom   40341/75

Column 6, line 48,   $Ci_2Hal_2$   should read   $Cu_2 Hal_2$.

Column 8, line 35,   "iron" should read -- ion --.

Column 26, line 5,   5-(5-(1,4-   should read   5-(5-(1,3-.

Signed and Sealed this

Twenty-sixth Day of June 1979

[SEAL]

Attest:

RUTH C. MASON
Attesting Officer

DONALD W. BANNER
Commissioner of Patents and Trademarks